United States Patent [19]

Ringermacher et al.

[11] Patent Number: 5,711,603
[45] Date of Patent: Jan. 27, 1998

[54] NONDESTRUCTIVE TESTING: TRANSIENT DEPTH THERMOGRAPHY

[75] Inventors: Harry I. Ringermacher, Bloomfield; Raymond J. Archacki, Jr., Wethersfield; William A. Veronesi, Hartford, all of Conn.

[73] Assignee: United Technologies Corporation, Hartford, Conn.

[21] Appl. No.: 739,572

[22] Filed: Oct. 30, 1996

[51] Int. Cl.$^6$ .................................................. G01N 25/72
[52] U.S. Cl. ........................... 374/5; 374/124; 364/507
[58] Field of Search ............................ 374/4, 5, 120, 374/121, 124, 137; 250/330, 332, 341.1, 342; 364/507, 557

[56] References Cited

U.S. PATENT DOCUMENTS

| | | |
|---|---|---|
| 4,768,158 | 8/1988 | Osanai ................................. 374/5 |
| 4,854,724 | 8/1989 | Adams et al. ....................... 374/5 |
| 5,032,727 | 7/1991 | Cox, Jr. et al. ..................... 374/5 |
| 5,246,291 | 9/1993 | Lebeau et al. ...................... 374/5 |
| 5,250,809 | 10/1993 | Nakata et al. ..................... 374/5 |
| 5,292,195 | 3/1994 | Crisman, Jr. ...................... 374/124 |
| 5,539,656 | 7/1996 | Annigeri et al. .................. 364/507 |
| 5,582,485 | 12/1996 | Lesniak ................................ 374/5 |

FOREIGN PATENT DOCUMENTS 2168494  6/1986  United Kingdom ................. 374/5

OTHER PUBLICATIONS

Vladimir P. Vavilov et al. "Thermal Characterization and Tomography of Carbon Fiber Reinforced Plastics Using Individual Identification Technique", *Materials Evaluation*, May 1996 vol. 54, No. 5, pp. 604–610.

*Primary Examiner*—G. Bradley Bennett
*Attorney, Agent, or Firm*—Pamela J. Curbelo

[57] ABSTRACT

The present invention relates to transient depth thermography; a nondestructive testing technique and system for locating flaws within an object. The system, which comprises a heater for heating the surface of the object; a recorder for recording pixel intensity for each pixel on the heated surface; a means for determining pixel contrast from the pixel intensity; and a means for determining the size and location of flaws within the object based upon the pixel contrast; monitors each pixels' contrast for successive thermal images and utilizes those pixel contrasts determining the location of a flaw within the object. The object surface and the respective underlying flaws can then be depicted on a color spectrum image print which correlates the flaw depth with a particular color.

14 Claims, 4 Drawing Sheets

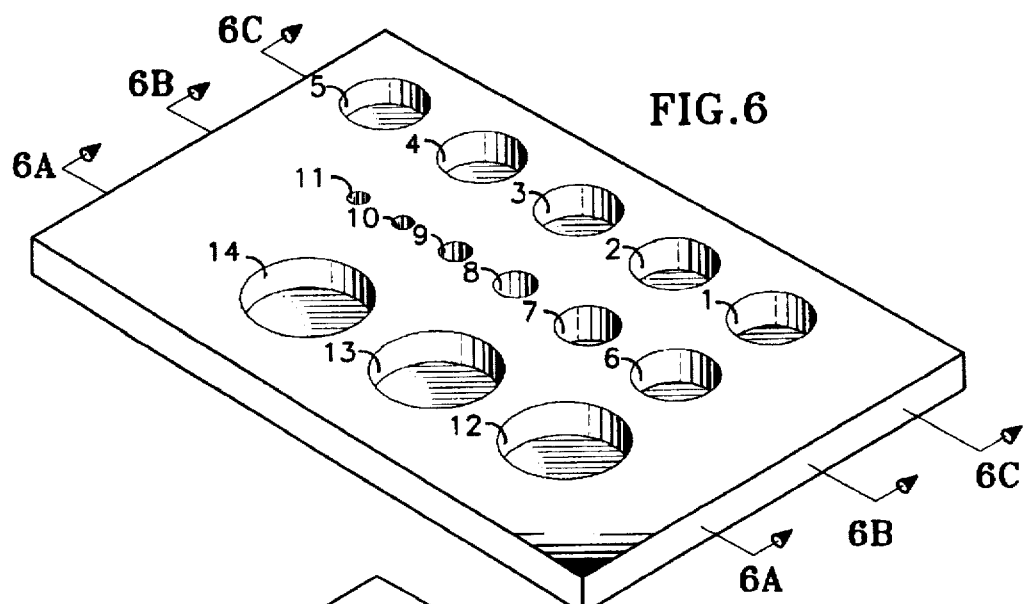
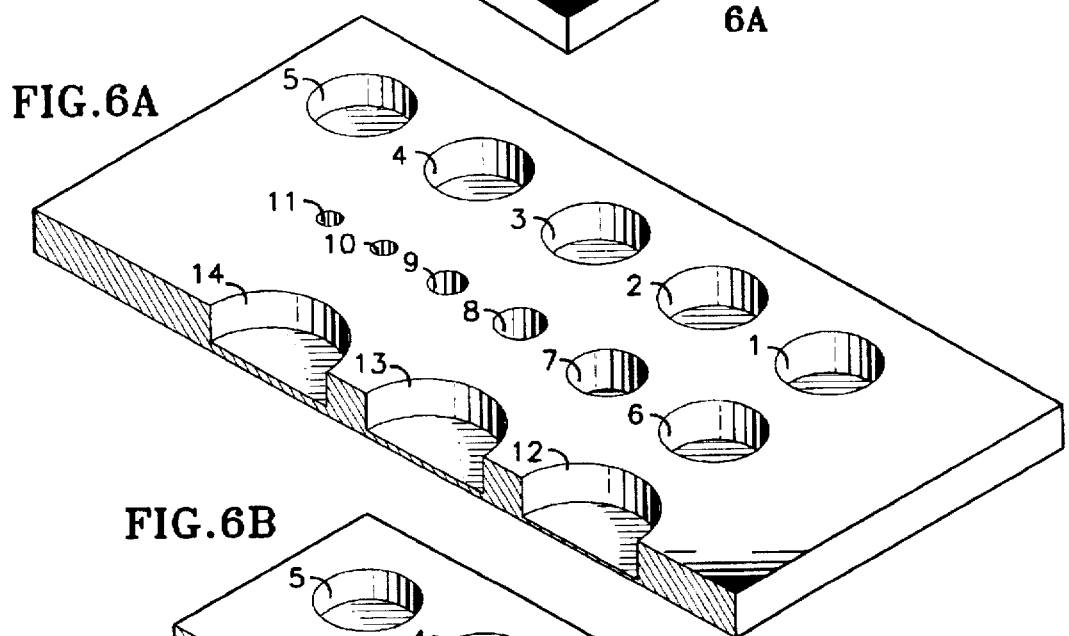
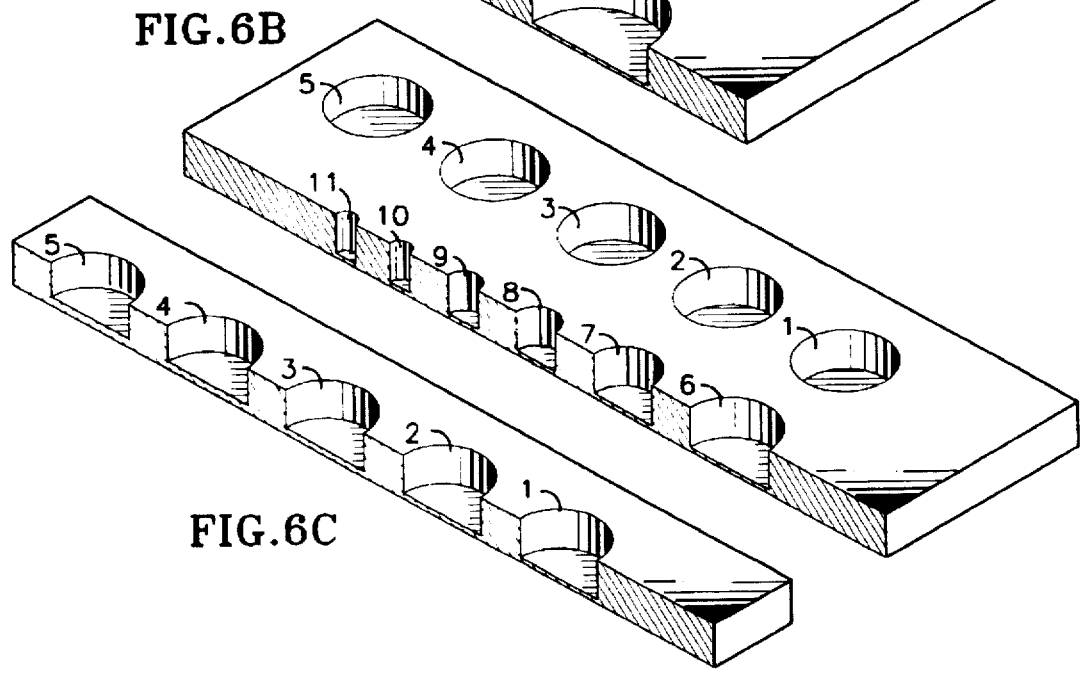

NONDESTRUCTIVE TESTING: TRANSIENT DEPTH THERMOGRAPHY

TECHNICAL FIELD

The present invention relates to nondestructive testing, and especially relates to nondestructive testing of an object to determine the depth and lateral position of subsurface flaws using transient thermography and to an imaging technique for displaying those flaws.

BACKGROUND OF THE INVENTION

The existence of a flaw within an object can be determined by various techniques, including transient thermography which relies upon the transfer of heat through an object over a period of time. One transient thermographic method comprises recording the temperature rise of each resolution element by capturing a series of image arrays using an infrared camera while heating the surface, and analyzing this temperature rise to identify if a transition to a linear temperature increase versus the square root of the heating time, occurs. This linear temperature increase indicates the existence of a flaw within the object. This determination is difficult as is and becomes more difficult with complex geometries and uneven heating.

Conventional transient thermography comprises analyzing individual infrared images, "snap-shots", of an object's previously heated surface as a function of time. Subsurface flaws are identified by "hot spots" in the image which emit greater intensity infrared radiation due to the heat's inability to disperse through the flaw. One problem with this conventional process is that the transient thermographic analysis is reduced to choosing a single snap-shot in time. The choice of which snap-shot to analyze is critical, and the best choice is based on many factors which cannot be controlled and are unknowns, such as depth and size of the flaw. If the incorrect snap-shot is chosen, flaws revealed on a previous or subsequent snap-shots, may not be detected.

To avoid the use of a snap-shot, an inspector watches a video replay of the recorded images and visually identifies bright spots indicative of flaws. The problem with this approach is that it is not readily automated, is highly operator dependent, is not readily applied to complex geometries or unevenly heated surfaces, and although a flaw may be detected with this approach, the actual depth and lateral position (hereinafter location) or size of the flaw cannot be accurately determined.

Conventionally, flaws are located through ultrasonic testing of the object. Essentially the object is struck with ultrasonic waves which penetrate the surface and are reflected by a flaw(s) within the object. Based upon the time required to receive a reflected wave, the location of the flaw can be determined.

Ultrasonic testing employs mechanical scanning with a transducer over the entire surface, with intimate sonic contact required. In order to allow intimate sonic contact, a stream of liquid couplant or total immersion of the object must be used; however, this is often unacceptable for material reasons. In addition to process problems, this technique is inefficient for testing large and/or complex objects. Mechanical scanning of a few square meters typically takes hours. Furthermore, scanning systems for geometrically complex parts are complex and expensive.

What is needed in the art is an automated, objective, transient thermographic depth imaging technique which can be employed with complex geometries and unevenly heated surfaces to accurately locate and size flaws within an object.

SUMMARY OF THE INVENTION

The present invention relates to a nondestructive testing technique and apparatus for locating flaws within an object. The apparatus comprises: a heater for heating the surface of the object; a recorder for recording intensity for each pixel of said heated surface; a means for determining pixel contrast from the surface intensity; and a means for determining the size and location of flaws within the object based upon the pixel contrast.

The method comprises the steps of: heating the surface of the object; recording successive thermal images of each resolution element of the surface over a period of time; determining each resolution element's (pixel's) contrast for each successive thermal image of the surface by determining the mean pixel intensity for that thermal image and subtracting said mean pixel intensity from the individual pixel's intensity; and determining the location of the flaw within the object based upon the pixel contrast.

BRIEF DESCRIPTION OF THE DRAWINGS

The file of this patent contains three drawings executed in color. Copies of this patent with color drawings will be provided by the Patent and Trademark Office upon request and payment of the necessary fee.

FIGS. 6, 6A, 6B, and 6C illustrate the test specimen and its relative dimensions for the flaws revealed in FIGS. 7, 8, and 9.

BEST MODE FOR CARRYING OUT THE INVENTION

Figure 1:
FIG. 1 is a graph of the intensity (temperature) versus time for an individual pixel (a) versus the mean pixel intensity (b).

The present invention is an automated nondestructive testing method which employs a transient thermographic analysis technique to determine the size and location of flaws in an object. This method which preferably uses time-temperature data to objectively detect flaws in an object by monitoring surface temperature variation of a heated object over time comprises: heating the object's surface and monitoring the thermal time constants for each pixel of the surface of the object. In the context of the present invention, a pixel is a rectangular picture element in an image array, while resolution element is a rectangular area of the surface of the object corresponding to a single pixel.

The device utilized to heat the object surface should be capable of heating the surface to a sufficient temperature to allow thermographic monitoring. Typically, thin objects, e.g. a thickness of about 0.125 inches (0.57 mm) or less, only require minimal heating, about 5° C. or less, with as little as about 1° C. possible. Meanwhile, thick objects may require significantly greater heating, e.g. about 20° C. for a 0.5 inch thick object. The surface factors, including color and emissivity, are also important in determining the degree to heat the object, while the physical properties establish the upper heating limit at a temperature which will not damage the object and/or the object's surface.

In order to accurately locate and determine the size of a flaw, the object surface should be heated to the desired temperature in a sufficiently short period of time so as to inhibit heating of the remainder of the object. Typically heating occurs in a fraction of a second for thin materials with up to a few minutes for thicker or larger materials; in a flash. If the heat penetrates the object, the accuracy of flaw detection near the object surface decreases. For example, a 0.125 thick graphite fiber and polymer composite can be heated for a few milliseconds with a 4 megawatt heat pulse from a flashlamp, while a 0.5 inch thick object should be heated for several seconds or even minutes with a 2 kilowatt heat pulse from a quartz lamp. Other possible heating methods include the use of microwaves, lasers, and other conventional heating means capable of high temperature, high speed heating.

Once the object's surface is heated, an infrared video camera records and stores successive thermal images of the objects surface, recording each pixel thereof. The number of images recorded depends upon the desired resolution of the resulting thermal image, the speed of the camera, and the time constant for the particular object (see below). About 10 images can be used to establish a thermal image, while about 25 images typically provides adequate resolution, and about 100 images establishes good resolution of the thermal image. Generally, up to about 500 images can be obtained at the current state of video technology, with above about 25 preferred.

When the heating device and video camera are located on the same side of the object, the time constant, $\tau_c$, used to establish the period of time for taking the thermal images, is obtained from Equation 1, where the depth is the thickness of the object.

$$\tau_c = \frac{4\,l^2}{\pi^2 \kappa} \quad (1)$$

$\tau_c$ = "characteristic" time constant
$\kappa$ = thermal diffusivity for the object
$l$ = depth When the camera and the heater are located on opposite sides of the object, the factor of 4 is dropped from Equation 1. Since thermal equilibrium is achieved within an object after approximately 5 characteristic time constants, the period of time used to take the thermal images is typically equivalent to about 3 to about 5 time constants, $\tau_c$, or more.

The video device is preferably a high speed focal plane array camera, or similar device, with a frame rate of at least about 60 flames per second up to about 250 frames per second or greater and a camera temperature sensitivity of at least about 0.01° C. to about 0.02° C. The minimal acceptable resolution is dependent upon the desired resolution of the final image print, with a resolution of 128×128 or greater pixels typically preferred.

Figure 2:
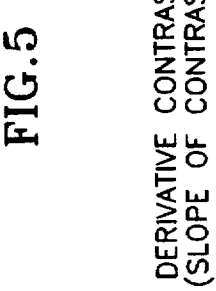
FIG. 2 is a graph of the pixel contrast versus time for the pixels of FIG. 1 to show the contrast peak.

The stored thermal images are used to determine each pixel's contrast by subtracting the mean pixel intensity for that image (point in time) (b) from the individual pixel's intensity (a) at that point in time. The contrast is then plotted versus time for each pixel. (see FIG. 2) The contrast over the flaw site peaks at a time which corresponds to when the image was taken by the video camera, the image number. Given the time at which a peak occurs, the depth of the flaw can be determined; a depth approximation is given by Equation 2:

$$l = \sqrt{\frac{\kappa \tau_{peak}}{3}} \quad (2)$$

$l$ = depth
$\tau_c$ = the "characteristic" time constant
$k$ = the "thermal diffusivity" of the medium measured in cgs units of cm²/sec.

Figure 3A:
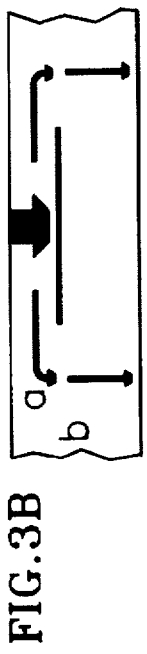
FIG. 3A is a cross-sectional view of an object revealing a thin delamination which is an example of a "through heat flaw" which allows through heat flow.
Figure 3B:
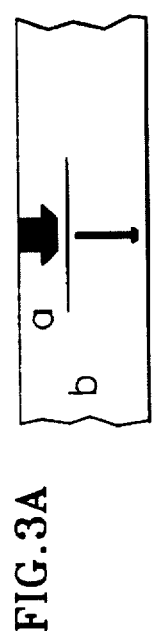
FIG. 3B is a cross-sectional view of an object revealing a thick delamination which is an example of a "lateral heat flaw" which requires mostly lateral heat flow.
Figure 5:
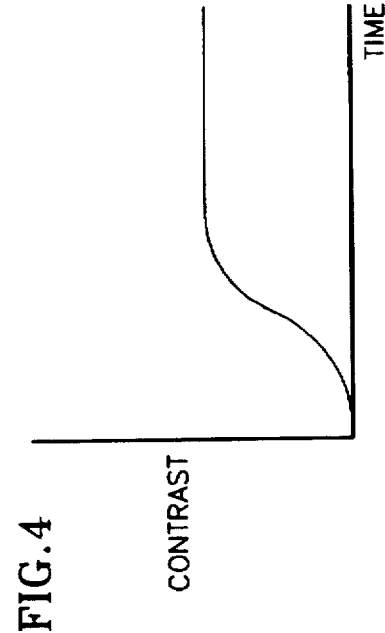
FIG. 5 is a graph of the derivative pixel contrast versus time for an individual pixel to show the derivative contrast peak for the "lateral heat flaw" from FIG. 4.

Equation 2 is particularly useful where the flaw's thickness does not force the heat to flow around the flaw; a "through heat" flaw (see FIG. 3A, a "through heat" flaw versus FIG. 3B, a "lateral heat" flaw).

Figure 4:
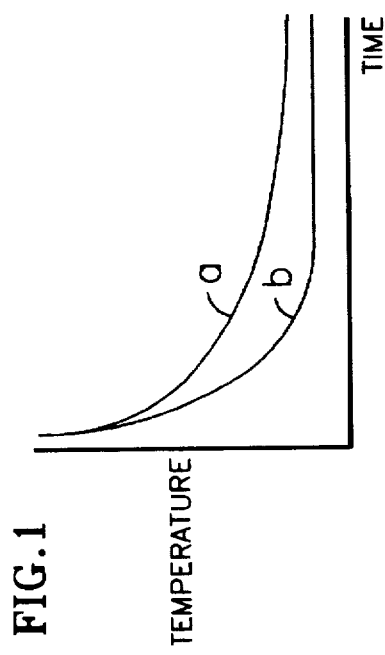
FIG. 4 is a graph of the pixel contrast versus time for an individual pixel where there is no contrast peak due to the type of flaw; a "lateral heat flaw".

Where, however, the rate of diffusion of the heat is faster around the flaw than through the flaw (FIG. 3B), the contrast peak is not evident from the graph of the pixel contrast (FIG. 4). Consequently, the time derivative of the contrast curve is taken in order to determine the derivative contrast peak. Depth of the "lateral heat" flaw can be determined from the peak time using the following Equation 3:

$$l = 0.524\pi \sqrt{\kappa \tau_i} \quad (3)$$

where $$\tau_c = 1.10\tau_i \quad (4)$$

$l$ = depth
$\tau_c$ = "characteristic" time constant
$\tau_i$ = the time of the derivative peak inflection
$k$ = the "thermal diffusivity" of the medium measured in cgs units of cm²/sec.

EXAMPLE

The accuracy of the present invention was established using an object having a series of carefully placed flat flaws. Referring to FIGS. 6, 6A, 6B, and 6C, flaws 1, 2, 3, 4, and 5 had the same diameter, 22 millimeters (mm), with varying depths, 1.3 mm, 1.6 mm, 1.9 mm, 2.2 mm, and 2.5 mm, respectively. Flaws 6, 7, 8, 9, 10 and 11 had the same depth, 1.3 mm, with varying diameters 22 mm, 16.5 mm, 11 mm, 8.25 mm, 5.5 mm, and 2.75 mm, respectively. Flaws 12, 13, and 14 had the same diameter, 33 mm, with varying depth, 1.3 mm, 1.9 mm, and 2.5 mm, respectively.

The test parameters were as follows: (1) each image frame consisted of N×N pixels (which corresponds to a resolution element on the object surface) where N was 256; (2) the number of image frames, Z, which typically ranges from 1 to 400 for N=128, and 1 to 200 for N=256, was 100; (3) each pixel occupied 2 bytes of storage and was represented by a 12-bit number from 0 to 4095, which represents the thermal radiation intensity.

Figure 7:
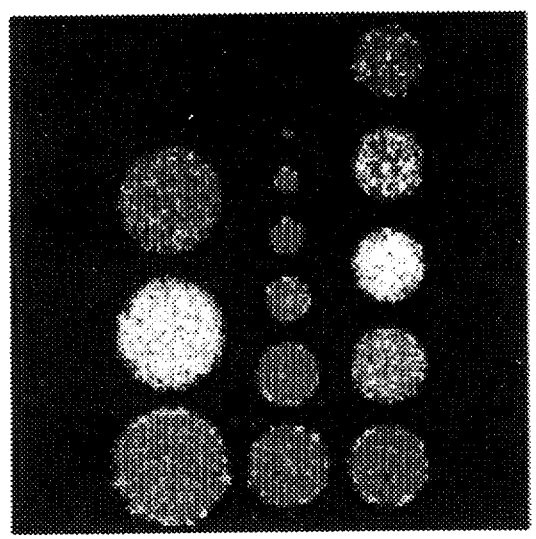
FIG. 7 is an image print of pixel intensity using the thermographic technique of the present invention.

The object was heated about 5° C. with a 4 megawatt heat pulse from a flashlamp for 0.010 seconds. Once heated, each resolution element intensity was recorded using a high speed focal plane array camera with a 256×256 pixel resolution operated for about 25 seconds, with each pixel represented by 12 bits. User parameters were determined and entered into the system, including: starting frame number to use for analysis (frame taken before the surface is heated are omitted); squelch constant; noise suppression (discards pixel locations whose absolute value of the peak minus the start or end value of the contrast curve is less than this constant); field of view (distance from the infrared camera to the object; allows scaling and therefore accurate size determination). The contrast of each pixel was determined with respect to the mean pixel intensity for the entire image using the difference between the pixel and the pixel mean times a fixed contrast gain. This operation was performed for each pixel on each image frame, producing a set of contrast curves. The derivative of each contrast curve was then determined using a 6-point difference method. Derivative contrast peak information was stored by saving the image frame number which produced the peak for each derivative contrast curve, or suppressing this information for pixel locations that exhibited low contrast or noise. The image frame location where the derivative contrast peak occurred was then used to determine the depth of the flaws which was shown visually using an intensity color spectrum as shown in FIG. 7. Note, the numbering of flaws shown in FIGS. 7, 8, and 9 is consistent with the number set forth in FIG. 6 which reveals the flaws detected in FIGS. 7, 8, and 9.

Figure 8:
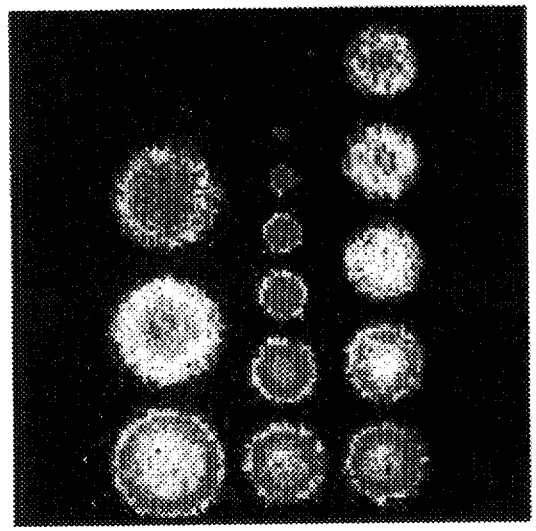
FIG. 8 is a present invention image print of pixel intensity using a prior art imaging technique.
Figure 9:
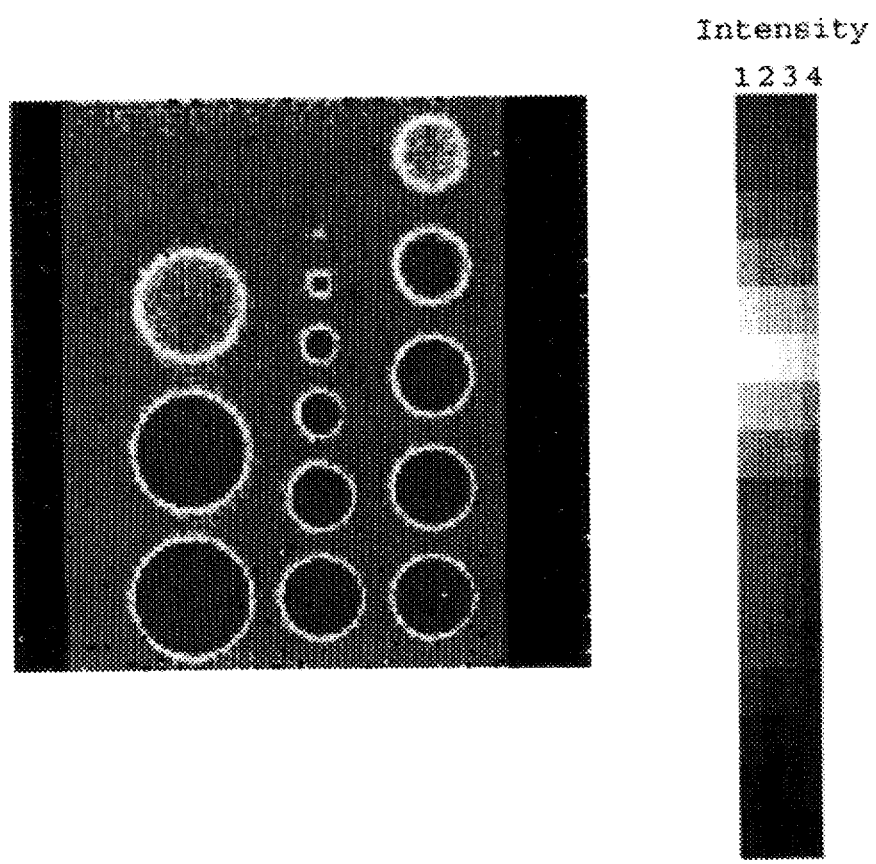
FIG. 9 is a present invention image print of pixel intensity representing temperature using prior art transient thermography.

The image print of the flaws was produced by assigning the stored peak frame numbers for each pixel to one of the colors in the 16 color palette shown on the right side of FIGS. 7, 8, and 9. This was done by taking the total number of colors (16) divided by the total number of frames (100) and then multiplying this by the peak frame number for the given pixel. This number was then rounded to an integer index into the color palette which selects one of the 16 possible colors for displaying this pixel. This process is then repeated for all of the pixel locations in the image. The image is further enhanced by using 4 intensity levels for each color, shown going from left to right on the color palette in FIGS. 7, 8 and 9. The largest peaks correspond to the highest intensity (level 1) of a given color and the smallest peaks correspond to the lowest intensity (level 4) of a given color. (see FIGS. 7, 8 and 9)

FIG. 8, in contrast, is an image print from the present invention depicting a prior art imaging technique which relies upon a snap-shot of the intensity profile. As is clear from this FIG. 8, the "snap-shot" was taken at a good point in time since all of the flaws are revealed. However, the majority of the flaws appear to be located at the same depth. Consequently, one can not determine the actual depth of any of the flaws. Furthermore, flaw 11 is only barely visible and difficult to identify as a flaw.

FIG. 9, which is also an image print using prior art transient thermography, similarly provides confusing information. In this figure the edges of the flaws appear shallower than the center of the flaws. Consequently, although the flaws are flat, they appear concave. Again, the depth of the flaws cannot be accurately determined.

The present invention provides numerous advantages over prior art non-destructive testing including: virtually eliminating human error, providing the ability to locate a flaw, and simplifying the image. The conventional prior art process relied upon an operator viewing numerous images or relied upon a single "snap shot" of the surface, i.e. human error, merely detected the existence of a flaw. The present invention allows for the accurate determination flaw depth and size, whereas the prior art could not resolve depth accurately.

We claim:

1. A method for detecting flaws in an object having a surface, said surface divided into an array of resolution elements, comprising the steps of:

a. heating the surface of the object;

b. recording a plurality of thermal images of each resolution element on said heated surface over a period of time, wherein each of said recorded resolution elements corresponds to a pixel;

c. determining individual pixel intensity for each of said pixels in each of said thermal images;

d. determining mean pixel intensity for each thermal image;

e. obtaining pixel contrast for each of said pixels in each of said thermal images subtracting said mean pixel intensity from said individual pixel's intensity; and d. determining depth of the flaw within the object based upon said pixel contrast.

2. A method as in claim 1 wherein the depth of the flaw is determined using the pixel contrast, obtaining the contrast peak, and thereby determining the location of the flaw using the following formula:

$$l = \sqrt{\frac{\kappa \tau_{peak}}{3}}$$

wherein $\tau_{peak}$ is the peak time, l is the depth of the flaw, and $\kappa$ is the thermal diffusivity of the object.

3. A method as in claim 1 wherein the depth of the flaw is determined by calculating the time derivative of the pixel contrast and obtaining the derivative contrast peak.

4. A method as in claim 3 wherein the depth of the flaw is determined by using the following formula:

$$l = \frac{\pi}{2} \sqrt{\kappa \tau_c}$$

wherein $\tau_c$ is the characteristic time constant, l is the depth of the flaw, and $\kappa$ is the thermal diffusivity of the object.

5. A method as in claim 3 wherein the depth of the flaw is determined by using the following formula:

$$l = \pi \sqrt{\kappa \tau_c}$$

wherein $\tau_c$ is the characteristic time constant, l is the depth of the flaw, and $\kappa$ is the thermal diffusivity of the object.

6. A method as in claim 1 further comprising producing an image print of the object which uses a color spectrum to display the depth and lateral position of the flaw.

7. An apparatus for locating flaws in an object having a surface which can be visualized as an array of pixels, comprising:

a. a heater for heating the surface of the object;

b. a recorder for recording pixel intensity;

c. a means for determining pixel contrast from said pixel intensity; and d. a means for determining depth and location of flaws within the object based upon said pixel contrast.

8. An apparatus as in claim 7 wherein said heater is a flash lamp, quartz lamp, microwave device, or laser.

9. An apparatus as in claim 7 wherein the depth of each flaw is determined from said pixel contrast using the following formula:

$$l = \sqrt{\frac{\kappa \tau_{peak}}{3}}$$

wherein $\tau_{peak}$ is the peak time, $l$ is the depth of the flaw, and $\kappa$ is the thermal diffusivity of the object.

10. An apparatus as in claim 7 wherein the depth of each flaw is determined from a derivative of said pixel contrast using the following formula:

$$l = \frac{\pi}{2} \sqrt{\kappa \tau_c}$$

wherein $\tau_c$ is the characteristic time constant, $l$ is the depth of the flaw, and $\kappa$ is the thermal diffusivity of the object.

11. An apparatus as in claim 7 wherein the depth of each flaw is determined from a derivative of said pixel contrast using the following formula:

$$l = \pi \sqrt{\kappa \tau_c}$$

wherein $\tau_c$ is the characteristic time constant, $l$ is the depth of the flaw, and $\kappa$ is the thermal diffusivity of the object.

12. An apparatus as in claim 7 further comprising a means for forming an image print which displays the depth and lateral position of the flaws using a color spectrum.

13. An object flaw display, said object having a surface, said surface represented by a plurality of resolution elements, comprising:

a. a color spectrum, wherein said spectrum correlates to depth;

b. a means for determining flaw depth below each resolution element of said object surface; and c. a means for displaying the object surface with the flaws depicted by the color which correlates to the flaw's depth.

14. A method as in claim 13 wherein said means for displaying displays the flaws on an image print.

* * * * *